United States Patent
Babizhayev (10) Patent No.: US 6,613,088 B1
(45) Date of Patent: Sep. 2, 2003

(54) COATED OPHTHALMIC AND IMPLANTABLE DEVICES AND METHODS FOR PRODUCING SAME

(76) Inventor: Mark A. Babizhayev, Ivanovskaya 20-74, Moscow 127434 (RU)

(*) Notice: Subject to any disclaimer, the term of this patent is extended or adjusted under 35 U.S.C. 154(b) by 0 days.

(21) Appl. No.: 09/509,218
(22) PCT Filed: Sep. 24, 1998
(86) PCT No.: PCT/IB98/01490
§ 371 (c)(1), (2), (4) Date: Mar. 24, 2000
(87) PCT Pub. No.: WO99/16390
PCT Pub. Date: Apr. 8, 1999

(30) Foreign Application Priority Data

Sep. 26, 1997 (MC) .................................... 2389

(51) Int. Cl.⁷ .............................................. A61F 2/16
(52) U.S. Cl. .................................................. 623/6.62
(58) Field of Search ................................ 623/6.56, 6.62

(56) References Cited

U.S. PATENT DOCUMENTS

| 4,718,905 A | 1/1988 | Freeman | 623/6 |
| 4,886,505 A | * 12/1989 | Haynes et al. | 604/265 |
| 5,147,125 A | * 9/1992 | Austin | 359/359 |
| 5,593,438 A | 1/1997 | Akhavi et al. | 623/6 |
| 5,607,463 A | 3/1997 | Schwartz et al. | 623/1 |
| 5,846,649 A | * 12/1998 | Knapp et al. | 428/334 |

FOREIGN PATENT DOCUMENTS

| EP | 280 215 | 8/1988 |
| EP | 295 397 | 12/1988 |
| WO | WO 93/09732 | 5/1993 |
| WO | WO 93/23092 | 11/1993 |

* cited by examiner

Primary Examiner—David H. Willse
Assistant Examiner—Jamie S. Blanco
(74) Attorney, Agent, or Firm—James C. Lydon (57) ABSTRACT

An implantable device and method for making the device. The device includes a metabolically-active coating on at least a portion of a surface of the device. Preferably, the coating has a thickness of less than about 500 angstroms. The coating improves the bio-compatibility of the device with the human body. The method is particularly applicable to implantable devices for implantation within the human eye, including intraocular lenses.

26 Claims, 3 Drawing Sheets

COATED OPHTHALMIC AND IMPLANTABLE DEVICES AND METHODS FOR PRODUCING SAME

This application is a U.S. National Stage of International application PCT/IB98/01490, filed Sep. 24, 1998 and published on Apr. 8, 1999 in the English Language.

BACKGROUND OF THE INVENTION

1. Field of the Invention

The present invention relates to devices that are adapted for implantation within the human body and methods for making such devices. More particularly, the present invention relates to a method for coating such devices and the devices coated thereby, wherein the coating increases the bio-compatibility and the medical usefulness of the device.

2. Description of Related Art

Artificial implantable devices, such as prosthetic devices or artificial eye lenses, have been implanted in humans for many years. For example, an artificial lens can be implanted in the posterior or anterior chamber of the human eye to restore vision of patients, as is done following cataract extraction. The function of the artificial lens, like the natural crystalline lens, is to maintain transparency and refract incidental light to focus the light on the retina for visual acuity.

Implantable artificial lenses, referred to as intraocular lenses (<<IOLs>>), have been made using many different designs. A common form of intraocular lens includes a central circular lens, frequently with flexible haptic loops radiating from the circumference of the lens to center the lens and maintain the position of the lens within the eye chamber.

The lens and haptic loops have been made from a number of different materials. Presently, polymethylmethacrylate (PMMA) is the most common material used for the lens portion of the IOL. Haptic loops have been made from a variety of materials, including plastics or metals. The haptic loops must be flexible and retain a spring-like quality to properly hold the lens in place without causing discomfort, such as from rubbing or tension on the ocular tissues. However, metal-loop lenses and poorly polished lenses can lead to chafting of the iris and related complications.

The tissues of the anterior segment of the eye and the corneal endothelium are bathed in an aqueous humor containing hydrogen peroxide ($H_2O_2$), lipid hydroperoxides and other reactive oxygen species. Natural crystalline lenses are anteriorly covered by a single layer of cuboidal epithelial cells which are highly metabolically active, and natural crystalline lenses that are healthy can tolerate substantial concentrations of such peroxides and lipid hydroperoxides without apparent damage. This ability of the natural lens is attributed to an active glutathione redox cycle. Typical concentrations of hydrogen peroxide in the aqueous humor of a healthy eye are on the order of 20 to 30 $\mu$M (micromoles per liter).

However, the average concentration of peroxides in cataract patients is elevated, typically to about 40 $\mu$M. Higher concentrations, such as 50 $\mu$M or higher, have been shown to cause significant corneal swelling and a decrease in the glutathione concentration. Concentrations of 50 $\mu$M or higher have also been shown to cause damage to DNA, including single strand breaks.

In addition to the foregoing complications, these oxygen derivatives and peroxide compounds are believed to contribute to pathological processes in ageing and systematic diseases, such as diabetes, artherosclerosis, chronic renal failure, inflammation and retinal degenerative diseases. IOLs that are implanted within the eye, for example after cataract extraction, do not have the ability to reduce or stabilize the concentration of these detrimental peroxide compounds. Therefore, the foregoing problems persist when the natural lens is replaced with an IOL. There is also evidence that PMMA lenses cause granulocytes to release significant amounts of oxygen radicals.

As it is discussed above, the anterior cuboidal epithelial cells of the natural crystalline lens which provide the antioxidant protection of the natural lens are usually removed during cataract extraction. However, the equatorial residual epithelial cells of the crystalline lens can spread to the posterior capsule, grow, and cause secondary opacification of the IOL after implantation. Further, a PMMA lens can cause a foreign body reaction accompanied by the formation of giant cells and macrophages on the IOL and acute chronic inflammation of the eye. The interaction between the ocular tissue and the artificial IOL can also be responsible for complications such as post operative inflammation, cell and pigment deposits on the lens, capsule opacification and macular oedema, a swelling of the macula of the retina.

U.S. Pat. No. 5,376,116 by Poler is directed to an intraocular lens device for impeding secondary growth within an eye, such as the growth of epithelial cells. It is disclosed that epithelial cell and protein strand development can be impeded by providing one or more metals and/or a basic salt in the environment or in the construction of the intraocular lens. It is believed that the metal and/or basic salt provide an electrolytic action within the capsule and that cell growth is thereby reduced. The changed pH, temperature and chemical balance that result allegedly reduce or eliminate-the ability of epithelial cells to multiply. When metal coatings are used, complicated schemes are used to produce patterns of at least two different metals on the lens surface. The device may be plated using known techniques and the thickness of the adhered coating is about 316 to 633 nm, as determined by interferometry.

U.S. Pat. No. 4,718,905 by Freeman is directed to a haptic element for an intraocular lens. The longevity of the haptic is enhanced by a bio-compatible and inert ion coating of the polypropylene haptic on the surfaces making tissue contact. The preferred coating elements are nitrogen, carbon, silicon and aluminum and the protective ion coating is applied by ion beam implantation.

Ion beam implantation has significant disadvantages. The implanted ions create a net positive surface charge which can facilitate the formation of free radicals. Further, the ions penetrate the surface of the device to a depth of up to 2 $\mu$m. This creates a new structure with decreased flexibility, stability and smoothness. Further, the process occurs at elevated temperatures which can damage the device. The process is also a <<line of sight>> process which is not readily adaptable to high volume production of devices.

It would be useful to provide a biologically compatible implantable device, such as an intraocular lens that mimics the capacity of the crystalline lens to withstand oxidative stresses and provide a reduction of peroxide compounds in ocular humors, thus preventing cellular disfunction and pathologies resulting from oxidative attack. It would be useful if such a device could be fabricated without sacrificing the desirable physical properties of the device, such as flexibility and smoothness.

In addition to the need for improved IOL devices, there is a need for improved bio-compatibility for other devices.

Because oxidative stress (e.g., an increase in peroxide concentration) can create internal disorders, there is a need for minimizing the adverse reaction of polymeric materials implanted into the human body. Such devices can include polymeric bone implants, medical sewing materials, and artificial polymeric vessels. Such devices can also include prosthetic heart devices, which should be resistant to thrombosis. In addition, there is a need for improved coatings for ophthalmic devices such as ophthalmic lenses and contact lenses, which are placed in contact with the human eye.

SUMMARY OF THE INVENTION

According to one aspect of the present invention, a device is provided which is adapted to be implanted within a human body wherein the device includes an outer surface having a coating deposited on at least a portion thereof by magnetron sputtering. Preferably, the coating has an average thickness of less than about 1 $\mu$m, more preferably less than about 500 angstroms. The coating can preferably include an element selected from the group consisting of platinum, palladium, manganese, nickel, gold, silver, rhodium, rhenium, cobalt, iridium, titanium, zirconium, niobium, tantalum, vanadium, aluminum, carbon, silicon, selenium, tin, boron, chromium, germanium, phosphorus, yttrium, hafnium, molybdenum, lanthanum, scandium, gadolinium, europium, terbium, neodymium, samarium, dysprosium, gallium, ytterbium, lutetium, erbium, thulium, calcium, magnesium, barium, cerium, zinc and indium, and compounds and combinations and alloys thereof, as well as compounds of nitrogen and oxygen. For some applications, copper and iron may also be useful. In a more preferred embodiment, the coating comprises platinum or an alloy thereof. In one embodiment, magnetron sputtering is applied for coating the outer surface of ophthalmic and implantable devices. Magnetron sputtering deposits the coating at much lower substrate temperatures (e.g., 20–50° C.), employing a super-cool sputtering processing method. The result is shorter batch processing times, combined with much better quality coatings applicable to organic/polymeric optical materials. Magnetron sputtering has distinct advantages over other vacuum technologies of coatings, for example electronic-beam, gun-evaporation, thermal evaporation, etc., since Magnetron-aided coating processing excludes the thermal load to the substrate. The device can be a prosthetic device or, in a preferred embodiment, can be an intraocular lens adapted to be implanted within a human eye. It should be understood that the term implantable devices can include partially implanted devices such as ophthalmic lenses and contact lenses for correcting vision.

According to another aspect of the present invention, an intraocular lens structure is provided. The intraocular lens includes a lens body adapted to be implanted within an eye and means for supporting the lens body within the eye wherein the supporting means includes at least one projection attached to the lens body wherein the projection has a first coating deposited thereon by magnetron sputtering. Preferably, the supporting means includes a plurality of haptic elements emanating from a circumference of the lens. In one embodiment, the lens body comprises polymethylmethacrylate. The lens structure can further include a second coating on the lens body wherein the second coating has an average thickness of less than about 500 angstrom. Preferably, the second coating has substantially the same composition as the first coating. Further, the second coating can be selected to reduce the transmission of ultraviolet light through the lens body. In a preferred embodiment, the projections are fabricated from polypropylene. The coating can optionally have a carbon film between the coating and the device to enhance the adherence of the coatings.

According to another aspect of the present invention, a method for treating an intraocular lens structure is provided. The method includes the step of magnetron sputtering a first metal onto the haptics to form a first metal coating on the haptics. Preferably, the coating has an average thickness of less than about 1 $\mu$m, more preferably less than about 500 angstroms.

The present invention also provides a method for decreasing the oxygen radical content and for reducing ocular inflammation. The method also reduces the levels of hydroperoxide compounds in the anterior chamber of an eye after implantation of an artificial intraocular lens. The method may also decrease the level of aldehyde and the products of oxidative modification of biomolecules in the anterior chamber. The method includes the steps of implanting an intraocular lens structure which includes a metal coating thereon having average thickness of less than about 500 angstroms, wherein the metabolically active coating includes a metabolically active element selected from the group consisting of platinum, palladium, manganese, nickel, gold, silver, rhodium, rhenium, cobalt, iridium, titanium, zirconium, niobium, tantalum, vanadium, aluminum, carbon, silicon, selenium, tin, boron, chromium, germanium, phosphorus, yttrium, hafnium, molybdenum, lanthanum, scandium, gadolinium, europium, terbium, neodymium, samarium, dysprosium, gallium, ytterbium, lutetium, erbium, thulium, compounds of nitrogen and oxygen, and indium, and compounds, combinations and alloys thereof.

DESCRIPTION OF THE INVENTION

The present invention is directed to devices which are adapted to be implanted within a human body and methods for making such devices. Such devices can include, but are not limited to, heart valves, prostheses of the abdominal aorta, artificial polymeric vessels, artificial articulations, medical sewing materials, wound dressings, adhesion materials polymeric bone implants, artificial skin implants, adsorbents, oxygen carriers, microcapsule polymeric materials for pharmacology, viscoelastic and bioadhesion materials and tooth crowns. Particularly preferred according to the present invention are devices which are implantable into the eye, including IOLs, keratoprotheses, drainages for glaucom surgery and the like. Further, as used herein, the term implantable devices can include partially implanted devices such as ophthalmic lenses and contact lenses for correcting vision.

According to the present invention, such devices are coated with a metabolically active coating which is deposited by magnetron sputtering on at least a portion of the surface of the device. The metabolically active coating is relatively thin and preferably has an average thickness of less than about 1$\mu$m, more preferably less than about 100 $\mu$m and even more preferably less than about 500 angstrom. The element which is coated onto the implantable device can be selected from platinum, palladium, manganese, nickel, gold, silver, rhodium, rhenium, cobalt, iridium, titanium, zirconium, niobium, tantalum, vanadium, aluminum, carbon, silicon, selenium, tin, boron, chromium, germanium, phosphorus, yttrium, hafnium, molybdenum, lanthanum, scandium, gadolinium, europium, terbium, neodymium, samarium, dysprosium, gallium, ytterbium, lutetium, erbium, thulium, calcium, magnesium, barium, cerium, zinc and indium, and compounds and combinations and alloys thereof, as well as compounds of nitrogen and oxygen. Metals such as platinum or vanadium can also be used in compounds containing them, such as $PtCl_2$, $VaO_2$, $PtCl_4$, $AgCl$, $MnO_2$ or $PdCl_2$. Other compounds such as $TiO_2$, $SiO_2$ and $Ta_2O_5$, can also be used. For certain implants, copper and iron may also be useful, although they are not preferred for use on an intraocular lens since they may induce inflammatory reactions dangerous to the retina. In a particularly preferred embodiment, the coating includes platinum or an alloy or compound of platinum. It is believed that platinum will form the finest grains in the coating.

Different materials may be useful depending on the particular application of the implanted device. For example, aluminum has the ability to block lipid peroxidation, and thus can be used effectively for IOL coatings. The lanthanide group of elements (e.g. lanthanum or cerium) can be used to react specifically with proteins which do not contain calcium ions, for example, albumin, lyzocyme, trypsin, chymotrypsin, chymotrypsinogen, and elastase. Such coatings can inhibit the activity of enzymes involved in the inflammatory response and block the adsorption of the proteins.

Perfluorocarbon coatings can be used for cordial valves and artificial vessels due to the high capacity of these polymeric compounds for binding oxygen and carbon dioxide. Coating with silicon compounds can also impart antioxidant activity to the polymeric surface.

It is often desirable in IOL devices that the coating on the device reduce the transmission of ultraviolet light which can be damaging to the retina. For example, the coating can be tinted using a yellowish color. Other colors can be used such as bluish colors to reduce fatigue while reading.

The process used according to the present invention to deposit the coating onto the surface of the implantable device is referred to as magnetron sputtering. Magnetron sputtering is a relatively low temperature process in which neutral atoms of an element (e.g. a metal) or dielectric material are deposited onto the surface of the device from a diffuse cloud of the atoms. This process advantageously minimizes specimen damage and forms a uniform thin film on the implantable device. Further, virtually any element or compound can be deposited using magnetron sputtering.

Because the coating is thin and uniform, the coating provides an implantable device having numerous advantages over prior art devices. Other techniques such as ion beam implantation implant ions (charged atoms) to a depth of up to 2 μm, thereby creating physical and chemical changes in the device, such as changes in elasticity. Further, ion beam implantation can create a net positive surface charge which can cause the release of highly reactive free radicals of oxygen into the surrounding environment. Such free radicals of oxygen can cause substantial damage to the surrounding tissues.

As is discussed above, the magnetron sputtering process is a low temperature process which advantageously minimizes specimen damage. For example, the preferred operating temperature for the magnetron sputtering process according to one embodiment of the present invention is from about 20° C. to about 50° C. In contrast, operating temperatures for ion beam implantation can approach 400° C. The process can generally be described as follows, with reference to FIG. 1. The device to be coated 10 is placed on a working table 12. Preferably, the table 12 is cooled, such as by water-cooling, and the table 12 is adjustable so that the distance between the device 10 and the metal source cathode 14 can be adjusted, if necessary. The table 12 is located within a working chamber 16 that is capable of being evacuated to form a substantial vacuum. The chamber is evacuated through an outlet 18 with a mechanical pump (not shown) to create a partial vacuum and the chamber 16 is then flushed several times with an inert gas, preferably argon, through a gas dosing valve 20 to substantially remove any contaminate materials, such as water vapor, from the chamber 16. The chamber 16 is then evacuated to reduce the pressure, for example to from about $10^{-5}$ to about $10^{-6}$ Torr. Thereafter, the inert gas is admitted into the chamber to increase the pressure, preferably to a range of from about $10^{-2}$ to about $10^{-3}$ torr.

Figure 1:
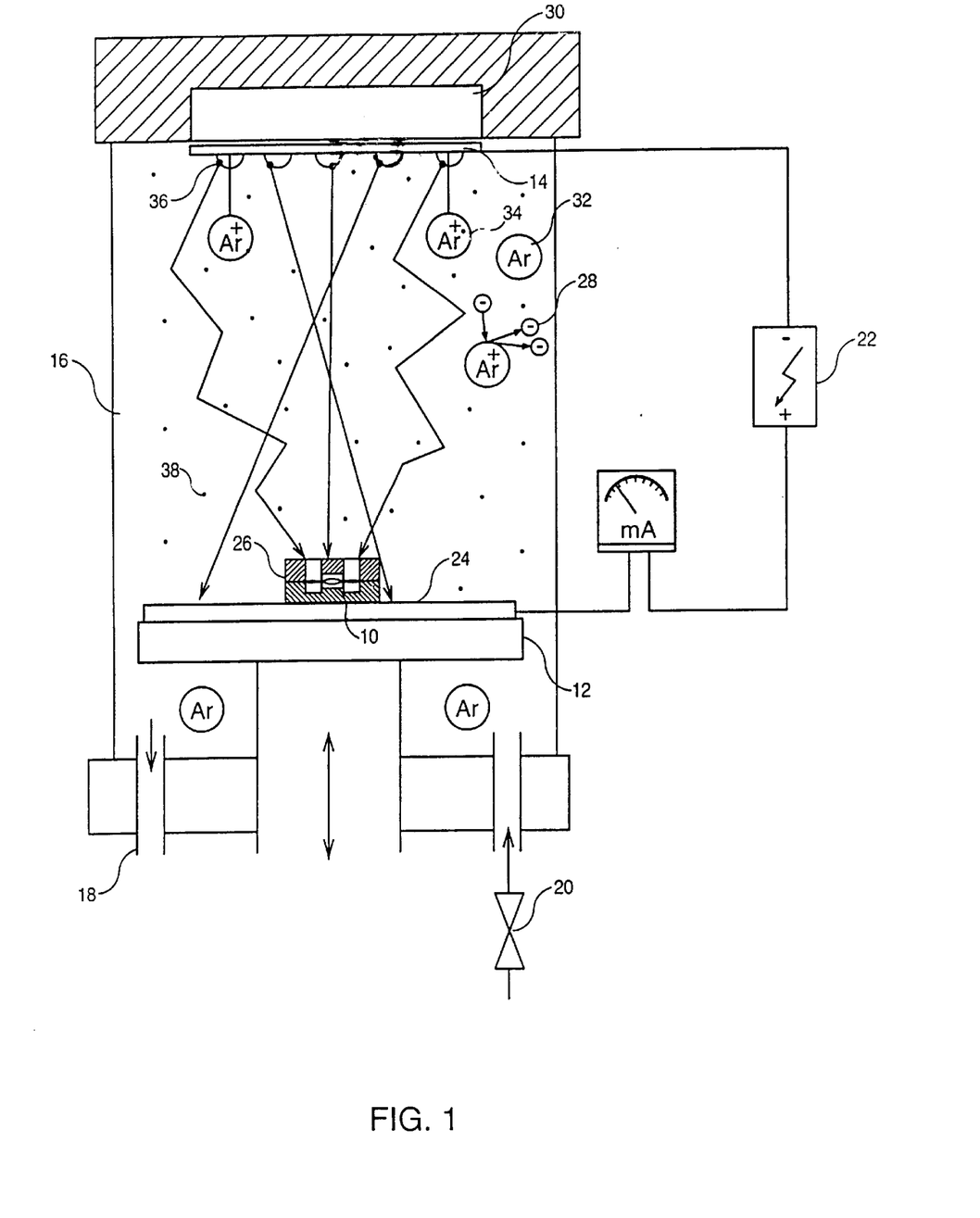
FIG. 1 illustrates an apparatus useful for carrying out the method of the present invention.

The chamber 16 also includes a metal source cathode 14 which includes in its composition the element to be deposited upon the implantable device 10. A high voltage is applied to the cathode 14 by a voltage source 22, for example about 5 kV, to form a sputtering current of, for example, about 50 mA. This produces a high voltage field between the cathode 14 and the anode 24.

The anode 24 is integral with the table 12 for supporting the device 10, which is typically placed in a specimen holder 26. The application of high voltage to the cathode 14 releases electrons 28 that are forced into a spiral path by a permanent magnet system 30 located either within or outside of the chamber 16. The electrons 28 collide with the inert gas molecules 32, positively charging the gas molecules to form ions 34. This cascading process causes a glow discharge plasma to form.

The positively charged ions 34 then accelerate toward and impact the cathode 14, thereby releasing one or more atoms 36, for example platinuim atoms. These atoms 36 collide with residual gas molecules 38 in the chamber, causing the atoms 36 then adhere to the surface of the implantable device 10, irrespective of the shape of the device. Nitrogen and oxygen compound can be applied to the device 10 by introducing the corresponding gas into the plasma, a method referred to as reactive magnetron sputtering.

The fine grained structure of the sputtered film is a function of the target material, the working distance, the gas pressure and sputtering current, as well as the process duration. Accordingly, it is preferred to use a sputtering current of about 50 ma. The working distance (between the target cathode and the device to be coated) is preferably from about 80 mm to about 150 mm to insure good adhesion of the film, particularly on the loops of an IOL device. The sputtering time is typically from about 5 to 20 seconds or possibly longer. For a particular device, the sputtering parameters must be chosen according to the heat load that the specimen can withstand. Heat-sensitive specimens such as plastic loops are sputter-coated from as long a working distance and as low a current as practicable. The process must be correspondingly longer to achieve the same desired film thickness. Further, reversing the voltage supply polarity allows the specimen table-anode to be placed on high voltage, enabling material to be sputtered off of the specimen, thereby providing an etching effect if desired. A shutter can be installed to protect the target from contamination during this process.

Figure 2:
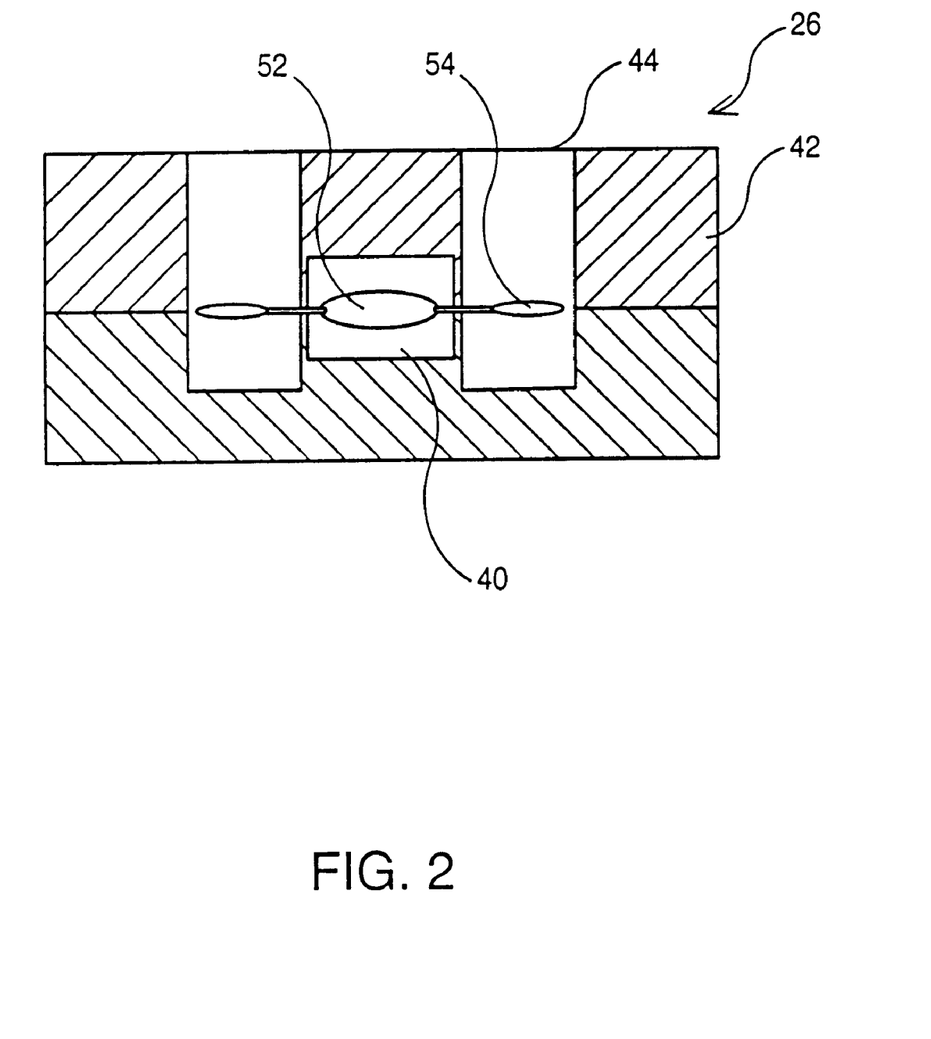
FIG. 2 illustrates a specimen holder useful in the apparatus illustrated in FIG. 1

A specimen holder 26 for coating the haptic elements of an IOL is illustrated in more detail in FIG. 2. The specimen holder 26 includes a chamber 40 which shields the lens 52 of the IOL. The specimen holder 26 includes a top portion 42 which advantageously shields the lens 52 while permitting coating of the haptics 54 by virtue of ports 44. The top portion 42 is preferably manufactured from an electrotransmitting material such as steel, copper or the like. Such a material advantageously reduces any incidental heating of the lens 52. It will be appreciated that a plurality of devices can be coated by placing any number of specimen holders within the chamber. Further, such specimen holders can be placed on a rotating table to adequately coat all specimens.

It has been found that when certain materials, such as gold or silver, are deposited using the magnetron sputtering process, extremely fine-grained films are not always formed due to the high surface diffusion of these materials. It has been found that this can be overcome by first coating the specimen with carbon. According to this embodiment, a double carbon thread evaporator is pushed into the vacuum chamber. The carbon thread is flash evaporated which coats the specimen with a thin, carbon film prior deposition of the primary coating. The carbon thread holder can then be pulled back from the chamber and the standard sputtering process can be initiated. Further, to reduce deterioration of the coating when the coating is exposed to atmospheric conditions, a second carbon film can be placed over the coating to act as a preservative for the coating. This second carbon film is applied by pushing the carbon thread evaporator back into the chamber and flashing the second carbon thread. This method advantageously permits carbon-metal-carbon coatings to be applied without breaking the vacuum.

When dielectric compounds are coated onto devices, a high-frequency magnetron sputtering process is preferred. A high-frequency process enables the application of dielectric compounds onto the surface of the polymeric lens with good adhesion. For processing with dielectric targets, the high-frequency voltage generator operates at a frequency of, for example, about 13.56 MHz and at an operating voltage of about 5 Kv. A sputtering current of from about 50 to about 200 mA is thereby formed.

In the case of a dielectric target under constant voltage supply, a layer of positively charged ions is rapidly created at the surface of the target which rejects the positively charged ions of plasma, making them unreactive to the target material and inhibiting the sputtering process. This would not be the case with metallic targets since negatively charged electrons derived from the conductive target neutralize the charge of the ions in the metal. There are no free available electrons in dielectric materials. In order to compensate for the surface positive charge of the ions at the dielectric target surface, the polarity of the target is changed under a high-frequency voltage signal from minus to plus. Under these conditions, the plasma electrons attach to the dielectric target and compensate the surface positive charge of the ions. The polarity at the target, in relation to the cathode, is changed from positive to negative and the sputtering process is conducted within the time period of the positive ion charge formation at the target surface. Thus, dielectric materials can be adequately sputtered.

In order to sputter comparatively thick films having a thickness of from about 100 nm to about 1 μm, it is desirable to pre-treat the substrate surface prior to the coating process in order to increase the adhesive strength of the coating.

This can be achieved by voltage shifting during the sputtering process. According to this embodiment, a shutter is installed in the vacuum chamber between the coating substrate and the target. The positively charged ions in the plasma move toward the substrate surface, enabling the surface contamination material of the substrate surface to be sputtered off. During this process, contaminants are removed from the surface layer and are removed onto the shutter. The cleaning process lasts, for example, for about 30 seconds. Upon completion of the cleaning procedure, a high-frequency voltage for a dielectric target or a constant voltage in the event of a metallic target is applied between the target and the anode. A low discharge plasma is switched on near the target and the shutter is pulled back from the chamber. The voltage between the target and the anode is gradually changed from the range of −400 volts to −2.5 kV to about −100 volts in a time period, for example, of about 60 seconds, which creates a voltage shift on the substrate. The applied conditions lead to the formation of a transition layer which consists of an atomic mixture of substrate and target material. This layer leads to an adhesive strength more suitable for the performance of further sputtering.

The present invention provides numerous advantages. When the coating is applied to the surface of a contact lens, the attachment of protein strands to the lens is significantly reduced. As is discussed above, the present invention is particularly advantageous for use with IOLs. The IOL according to the present invention catalyzes the reduction of peroxide compounds to decrease their levels within the aqueous humor. Further, the coatings also scavenge toxic free radicals of oxygen, thus preventing cellular disfunction resulting from oxidative attack. The coating devices, especially coated IOLs, reduce the post-operative (ocular) inflammation due to the inhibitory action of noble metals such as gold, silver or platinum to inflammative reaction. In essence, this device of mimics the function of glutathione peroxidase and other defences of the natural crystalline lens against hydrogen peroxide and other aggressive oxidants. It is not believed that prior art artificial lenses have sufficiently addressed this problem.

The coating also advantageously reduces epithelial cell development on the IOL surface. In addition, the coating can *he be formulated to reduce the glare effect of IOLs and can screen out ultraviolet light.

The mechanism that reduces the peroxide concentration is believed to be the catalyzing affect of a thin layer of metal. Using platinum as an example, the metal is believed to catalyze the peroxide reduction to form molecular products of alcohol and water as follows:

(1)

(2)

(3)

In prior devices such as those discussed above, the ions are penetrated to a depth of up to 2 μm or more in the thickness of the device (such as the haptic loops) and this condition does not permit the interaction of ions with the outer space peroxide compounds. Further, the charge ion coating can itself produce free radicals of oxygen in the surrounding medium.

Figure 3:
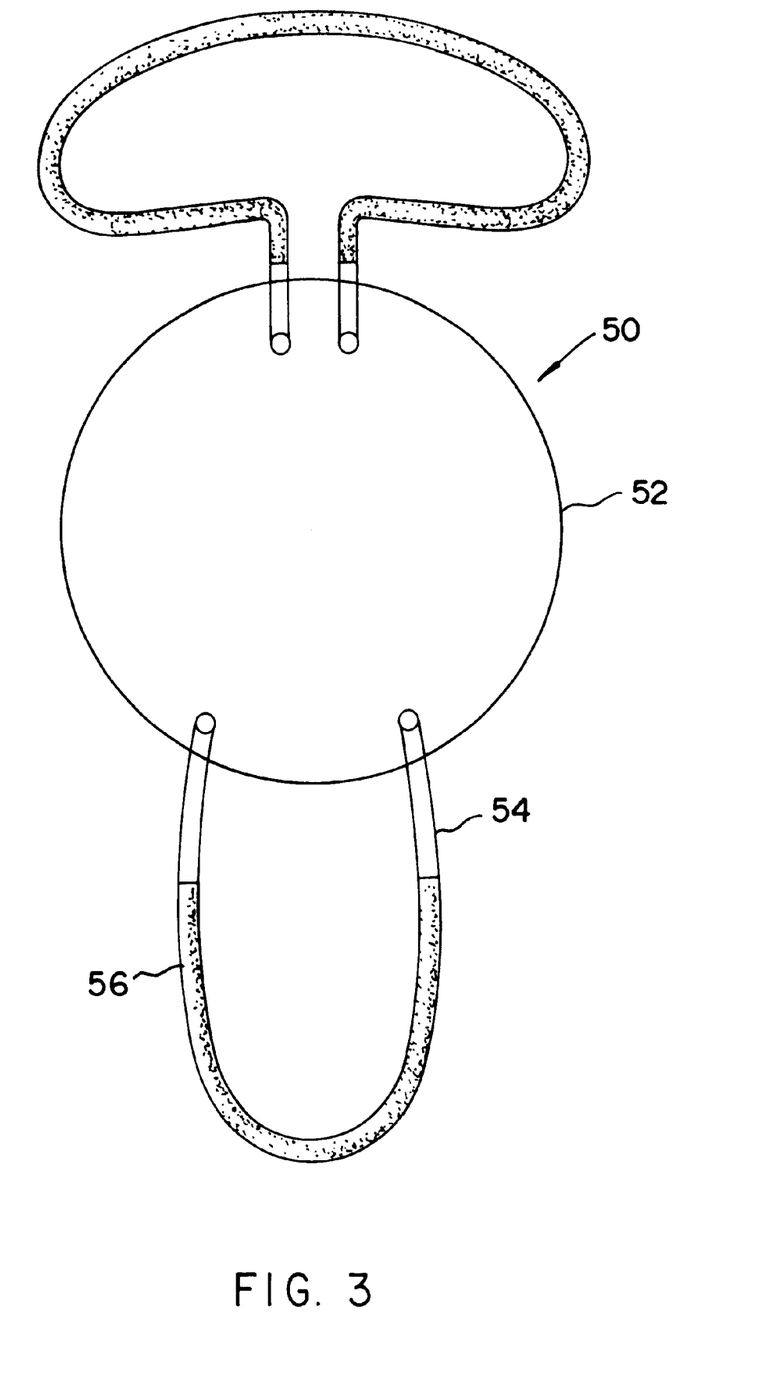
FIG. 3 illustrates an implantable intraocular lens according to an embodiment of the present invention

An IOL is illustrated in FIG. 3. The IOL 50 includes a lens 52 and a plurality of haptic loops 54 emanating from the circumference of the lens. Typically, the lens 52 is fabricated from a polymer material such as PMMA. The haptic loops 54 can be made from material such as polypropylene since PMMA is generally too stiff to be used as the haptic material. As illustrated in FIG. 3, a portion of the haptic loops 54 are coated with a thin coating of platinum 56. Although illustrated as a lens including haptic loops 54, it is also understood that other means to hold the lens 52 in place can be used, such as foot plates or the like.

EXAMPLES

1. Estimating Leakage of Sputtered Platinum From a Lens Haptic

In order to confirm that deposited platinum according to the present invention does not substantially leak into water solutions from the haptic surface of an IOL, a study of the coatings was performed by the addition to water of $NH_4Cl$, HCl, NaOH and $NH_4OH$. For this purpose, the incubation period of the sputtered samples was three months at a temperature of 20–25° C. with the addition of saline (0.9% NaCl) to the solutions. The solutions were subjected to slow stirring pH ranges were adjusted as follows:

TABLE I

| Incubation Solutions | |
|---|---|
| pH Value | pH Adjusting Salt |
| 4.0 | HCl ($10^{-4}$ M) |
| 6.0 | HCl, $NH_4Cl$ |
| 8.0 | $NH_4OH$ |
| 10.0 | NaOH |
| 12.0 | NaOH ($10^{-2}$ M) |

The possibility of formation of platinum-containing salts or the release of unbounded platinum atoms in the medium was measured after 1, 5 and 10 days, and after 1, 2 and 3 months of incubation. The results showed no leakage of the sputtered platinum from the IOLs. The testing procedure used is capable of detecting a platinum concentration of $10^{-7}$ to $10^{-8}$ percent or higher.

2. Peroxidase Activity

The peroxidase activity of an IOL of the present invention was determined using hydrogen peroxide or organic hydroperoxide as a substrate. A net decrease in NADPH (reduced nicotinamide adenine dinucleotide phosphate), which is monitored spectrophotometrically at a wavelength of 340 nm, is an accurate measure of the peroxidase activity of the lens since the IOL is used to reduce the peroxide compounds with NADPH as a cofactor.

An assay mixture (2.9 ml) consisted of 2.6 ml of 0.05 M phosphate buffer (pH 7.0) and 0.1 ml of 8.4 mM NADPH. The lens was allowed to equilibrate in the mixture for 10 minutes at 37° C. The reaction was initiated by the addition of either 0.1 ml of 2.2 mM $H_2O_2$ or 0.1 ml of 20 mM tert-butyl hydroperoxide. A decrease in the optical density at a wavelength of 340 nm was observed continuously for 20 min as compared to a control in which all the ingredients of the assay mixture were present without the IOL. The peroxidizing activity is expressed as $\mu$mols of substrate utilised/lens per min using the molar extinction coefficient value of 6.1 $mM^1cm^{-1}$. The glutathione peroxidase activity of a homogenized crystalline human lenses was also measured.

The results illustrating a peroxide-metabolizing activity of the IOL's are presented in Table II. The relative activities of the IOLs tested are compared to that of GSH (reduced glutathione) peroxidase of the crystalline human lenses at different stages of cataract formation.

TABLE II

Peroxide-Metabolizing Activity of Lenses

| | | PROXIDASE ACTIVITY | |
|---|---|---|---|
| Lens | Area of Opacity[1] | $H_2O_2$ | TBHP[2] |
| Transparent human lens (n = 10) | 0 to 0.1 | 1.3 ± 0.2 | 0.51 ± 0.04 |
| Immature human cataract (n = 9) | 0.1 to 0.7 | 0.98 ± 0.21 | 0.404 ± 0.049*** |
| Mature human cataract (n = 8) | 0.8 to 1.0 | 0.92 ± 0.21 | 0.195 ± 0.047* |
| Artificial intraocular lens (n = 5) | 0.0 to 0.0 | 1.1 ± 0.2 | 0.88 ± 0.02** |

Notes:
[1]Ratio of area of zone of opacity to total area of lens measured morphometrically;
[2]In $\mu$mol NADPH/min per lens with $H_2O_2$ or tertbutylhydroperoxide (TBHP) as the substrate measured at 37° C.;
*P < 0.001 compared with transparent human lens
**P > 0.001 compared with mature human cataract
***P < 0.1 compared with transparent human lens
P = the statistical significance of the differences
n = number of samples As can be seen from Table II, the IOLs having metabolic activity according to the present invention degrade the molecules of H2O2 without any loss of catalytic activity, as compared to the transparent human crystalline lens. The catalytic activity towards organic hydroperoxides, including lipid hydroperoxides, is even higher than that of the transparent human lens and of the mature human cataract lens. The IOLs are able to metabolize the phospholipid hydroperoxides.

Thus, it can be expected that the implantation of IOLs with metabolic activity will improve the capability of the surrounding ocular tissues to withstand oxidative stress induced in ocular humors by the photochemical and other metabolic reactions.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:
1. A device adapted to be implanted within a human body, said device comprising an outer surface, wherein said outer surface has a first coating deposited on at least a portion thereof by magnetron sputtering,
   wherein said first coating has an average thickness of less than about 500 angstroms,
   wherein said first coating comprises an element selected from the group consisting of platinum, palladium, manganese, nickel, gold, silver, rhodium, rhenium, cobalt, iridium, titanium, zirconium, niobium, tantalum, vanadium, aluminum, carbon, silicon, selenium, tin, boron, chromium, germanium, phosphorus, yttrium, hafnium, molybdenum, lanthanum, scandium, gadolinium, europium, terbium, neodymium, samarium, gallium, dysprosium, ytterbium, lutetium, erbium, thulium, compounds of nitrogen and oxygen, and indium, and compounds and combinations and alloys thereof, with the proviso that there is a second coating of another element when said first coating comprises carbon, wherein said first coating does not release substantial amounts of said element into an aqueous environment, and wherein said device will react as a body enzyme with deleterious peroxide compounds and free radical oxygen species in body fluids and tissue when said device is implanted into said human body.

2. A device as recited in claim 1, wherein said first coating comprises platinum or a compound or an alloy thereof.

3. A device as recited in claim 1, wherein said device is adapted to be implanted within a human eye.

4. A device as recited in claim 3, wherein said device is an intraocular lens.

5. A device as recited in claim 1, wherein said device is a prosthetic device.

6. A device as recited in claim 1, wherein said device is used for ophthalmic correction with ophthalmic lenses.

7. An intraocular lens structure, comprising:
(a) a lens body adapted to be implanted within an eye; and
(b) means for supporting said lens body within the eye; wherein said supporting means comprises at least one projection attached to said lens body, said projection having a first coating deposited thereon by magnetron sputtering, and
wherein said first coating has an average thickness of less than about 500 angstroms,
wherein said first coating does not release substantial amounts of said coating into an aqueous environment, and
wherein said intraocular lens structure will react as a body enzyme with deleterious peroxide compounds and free radical oxygen species in body fluids and tissue when said intraocular lens structure is implanted into said eye.

8. An intraocular lens structure as recited in claim 7, said wherein means for supporting comprises a plurality of haptic elements emanating from a circumference of said lens.

9. An intraocular lens structure as recited in claim 7, wherein said first coating comprises an element selected from the group consisting of platinum, palladium, manganese, nickel, gold, silver, rhodium, rhenium, cobalt, iridium, titanium, zirconium, niobium, tantalum, vanadium, aluminum, carbon, silicon, selenium, tin, boron, chromium, germanium, phosphorus, yttrium, hafnium, molybdenum, lanthanum, scandium, gadolinium, europium, terbium, neodymium, samarium, dysprosium, gallium, ytterbium, lutetium, erbium, thulium, compounds of nitrogen and oxygen, and indium, and compounds and combinations and alloys thereof.

10. An intraocular lens structure as recited in claim 7, wherein said first coating comprises platinum or a compound or alloy thereof.

11. An intraocular lens structure as recited in claim 7, wherein said lens body comprises polymethylmethacrylate.

12. An intraocular lens structure as recited in claim 7, wherein said lens body comprises a second coating having an average thickness of less than about 500 Angstrom.

13. An intraocular lens structure as recited in claim 12, wherein said second coating has substantially the same composition as said first coating.

14. An intraocular lens structure as recited in claim 12, wherein said second coating reduces the transmission of ultraviolet light through said lens body.

15. An intraocular lens structure as recited in claim 7, wherein said projection comprises polypropylene.

16. An intraocular lens structure as recited in claim 7, wherein said projection comprises a carbon film beneath said first coating.

17. An intraocular lens structure, comprising:
(a) a lens body adapted to be implanted within an eye; and
(b) a plurality of haptic loops radiating from said lens body that are adapted to support and position said lens within the eye; wherein said haptic loops comprise a first metabolically active coating having a thickness of less than about 500 angstroms, and
wherein said intraocular lens structure will react as a body enzyme with deleterious peroxide compounds and free radical oxygen species in body fluids and tissue when said intraocular lens structure is implanted into said eye.

18. An intraocular lens structure as recited in claim 17, wherein said coating comprises platinum or a compound or an alloy thereof.

19. An intraocular lens structure as recited in claim 17, wherein said coating is deposited by magnetron sputtering.

20. An intraocular lens structure as recited in claim 17, wherein said lens body comprises a second metabolically active coating having a thickness of less than about 500 angstrom.

21. A method for treating an intraocular lens structure having haptics prior to placement of the lens in an eye, comprising the step of magnetron sputtering a first element selected from the group consisting of platinum, palladium, manganese, nickel, gold, silver, rhodium, rhenium, cobalt, iridium, titanium, zirconium, niobium, tantalum, vanadium, aluminum, carbon, silicon, selenium, tin, boron, chromium, germanium, phosphorus, yttrium, hafnium, molybdenum, lanthanum, scandium, gadolinium, europium, terbium, neodymium, samarium, dysprosium, gallium, ytterbium, lutetium, erbium, thulium, compounds of nitrogen and oxygen, and indium, and combinations and compounds and alloys thereof onto said haptics to form a first metabolically active coating on said haptics,
wherein said first metabolically active coating has an average thickness of less than about 500 angstroms,
wherein first metabolically active coating does not release substantial amounts of said first element into an aqueous environment, and
wherein said intraocular lens structure, after said treatment, will react with as a body enzyme with deleterious peroxide compounds and free radical oxygen species in body fluids and tissue when said intraocular lens structure is implanted into said eye.

22. A method as recited in claim 21, wherein said first element comprises platinum or a compound or an alloy thereof.

23. A method as recited in claim 21, wherein said method further comprises the step of magnetron sputtering a second element selected from the group consisting of platinum, palladium, manganese, nickel, old, silver, rhodium, rhenium, cobalt, iridium, titanium, zirconium, niobium, tantalum, vanadium, aluminum, carbon, silicon, selenium, tin, boron, chromium, germanium, phosphorus, yttrium, hafnium, molybdenum, lanthanum, scandium, gadolinium, europium, terbium, neodymium, samarium, dysprosium, gallium, ytterbium, lutetium, erbium, thulium, compounds of nitrogen and oxygen, and indium, and compounds and combinations and alloys thereof onto said lens body to form a second metabolically active coating thereon.

24. A method for decreasing the oxygen radical content and reducing the levels of hydroperoxide compounds in the anterior chamber of an eye after implantation of an artificial intraocular lens, comprising the step of implanting an intraocular lens structure within said eye wherein said intraocular lens structure comprises at least a first, metabolically active coating having metabolically active element selected from the group consisting of platinum, palladium, manganese, nickel, gold, silver, rhodium, rhenium, cobalt, iridium, titanium, zirconium, niobium, tantalum, vanadium, aluminum, carbon, silicon, selenium, tin, boron, chromium, germanium, phosphorus, yttrium, hafnium, molybdenum, lanthanum, scandium, gadolinium, europium, terbium, neodymium, samarium, gallium, dysprosium, ytterbium, lutetium, erbium, thulium, compounds of nitrogen and oxygen, and indium, and compounds and combinations and alloys thereof,     wherein said coating has an average thickness of less than about 500 angstroms, and     wherein said coating does not release substantial amounts of said element into an aqueous environment, and     wherein said intraocular lens structure will react as a body enzyme with deleterious peroxide compounds and free radical oxygen species in body fluids and tissue when said intraocular lens structure is implanted into said eye.

25. A method as recited in claim 24, wherein said coating comprises platinum or a compound or an alloy thereof.

26. A method as recited in claim 24, wherein said lens structure comprises haptics and said coating substantially covers said haptics.

\* \* \* \* \*